(12) United States Patent
Valeri et al.

(10) Patent No.: US 10,474,423 B2
(45) Date of Patent: Nov. 12, 2019

(54) SYSTEMS AND METHODS FOR SOUNDSCAPE SELECTION IN AUTONOMOUS VEHICLES

(71) Applicant: GM GLOBAL TECHNOLOGY OPERATIONS LLC, Detroit, MI (US)

(72) Inventors: Frank C. Valeri, Novi, MI (US); Scott M. Reilly, Southfield, MI (US); Eli Tzirkel-Hancock, Ra'Anana (IL)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 120 days.

(21) Appl. No.: 15/622,652

(22) Filed: Jun. 14, 2017

(65) Prior Publication Data

US 2018/0364966 A1    Dec. 20, 2018

(51) Int. Cl.
*G06F 3/16*    (2006.01)
*H04R 29/00*    (2006.01)
*A61M 21/02*    (2006.01)

(52) U.S. Cl.
CPC ........... *G06F 3/165* (2013.01); *H04R 29/001* (2013.01); *A61M 21/02* (2013.01)

(58) Field of Classification Search
CPC .. A61M 21/02; G07C 5/0841; B60W 50/082; G06F 3/165; H04R 29/001
See application file for complete search history.

(56) References Cited

U.S. PATENT DOCUMENTS

| | | | | |
|---|---|---|---|---|
| 2013/0197715 A1* | 8/2013 | Otanez | ................ | B60W 50/082 701/2 |
| 2015/0313475 A1* | 11/2015 | Benson | ................ | A61B 5/6893 297/217.3 |
| 2015/0371457 A1* | 12/2015 | Bakfan | ................ | G07C 5/0841 701/29.3 |
| 2016/0103833 A1 | 4/2016 | Sanders et al. | | |
| 2018/0344968 A1* | 12/2018 | Gordon | ................. | A61M 21/02 |

OTHER PUBLICATIONS

Rathore et al., Integrating biometric sensors into automotive Internet of Things, 2014, IEEE, p. 178-181 (Year: 2014).*

* cited by examiner

*Primary Examiner* — McDieunel Marc
(74) *Attorney, Agent, or Firm* — Lorenz & Kopf, LLP (57) ABSTRACT

Systems and method are provided for controlling a vehicle. A method of soundscape selection in a vehicle includes receiving a number of biometric parameters from sensors provided within an interior of the vehicle, and determining a state-of-mind of an occupant within the interior of the vehicle based on the biometric parameters. The method further includes selecting, with a soundscape determination module including a processor, a soundscape responsive to the state of mind of the occupant, and providing to the vehicle a set of vehicle parameters based on the selected soundscape.

17 Claims, 6 Drawing Sheets

FIG. 5 the page content # SYSTEMS AND METHODS FOR SOUNDSCAPE SELECTION IN AUTONOMOUS VEHICLES

TECHNICAL FIELD

The present disclosure generally relates to autonomous vehicles, and more particularly relates to systems and methods for selecting interior soundscapes in such vehicles.

BACKGROUND

An autonomous vehicle is a vehicle that is capable of sensing its environment and navigating with little or no user input. It does so by using sensing devices such as radar, lidar, image sensors, and the like. Autonomous vehicles further use information from global positioning systems (GPS) technology, navigation systems, vehicle-to-vehicle communication, vehicle-to-infrastructure technology, and/or drive-by-wire systems to navigate the vehicle.

While recent years have seen significant advancements in autonomous vehicles, such vehicles might still be improved in a number of respects. For example, currently-known autonomous vehicles often do not provide an occupant the capability to modify the overall sound conditions (i.e., the "soundscape") experienced by occupants within the interior of the vehicle.

Accordingly, it is desirable to provide systems and methods for selecting interior soundscapes in autonomous vehicles. Furthermore, other desirable features and characteristics of the present invention will become apparent from the subsequent detailed description and the appended claims, taken in conjunction with the accompanying drawings and the foregoing technical field and background.

SUMMARY

Systems and method are provided for controlling an autonomous vehicle. In one embodiment, a method of soundscape selection in a vehicle includes receiving a plurality of biometric parameters from sensors provided within an interior of the vehicle, and determining a state-of-mind of an occupant within the interior of the vehicle based on the biometric parameters. The method further includes selecting, with a soundscape determination module including a processor, a soundscape responsive to the state of mind of the occupant, and providing to the vehicle a set of vehicle parameters based on the selected soundscape.

In one embodiment, an autonomous vehicle includes one or more sensors provided within an interior of the autonomous vehicle, wherein the sensors are configured to observe an occupant within the interior of the autonomous vehicle and produce a plurality of biometric parameters associated therewith. The autonomous vehicle also includes a state of mind determination module, including a processor, configured to determine a state-of-mind of an occupant within the interior of the vehicle, and a soundscape determination module, including the processor, configured to select a soundscape responsive to the state of mind of the occupant and provide to the vehicle a set of vehicle parameters based on the selected soundscape.

DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the application and uses. Furthermore, there is no intention to be bound by any expressed or implied theory presented in the preceding technical field, background, brief summary, or the following detailed description. As used herein, the term "module" refers to any hardware, software, firmware, electronic control component, processing logic, and/or processor device, individually or in any combination, including without limitation: application specific integrated circuit (ASIC), a field-programmable gate-array (FPGA), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure.

For the sake of brevity, conventional techniques related to audio processing, facial recognition, signal processing, data transmission, signaling, control, machine learning, image analysis, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Figure 1:
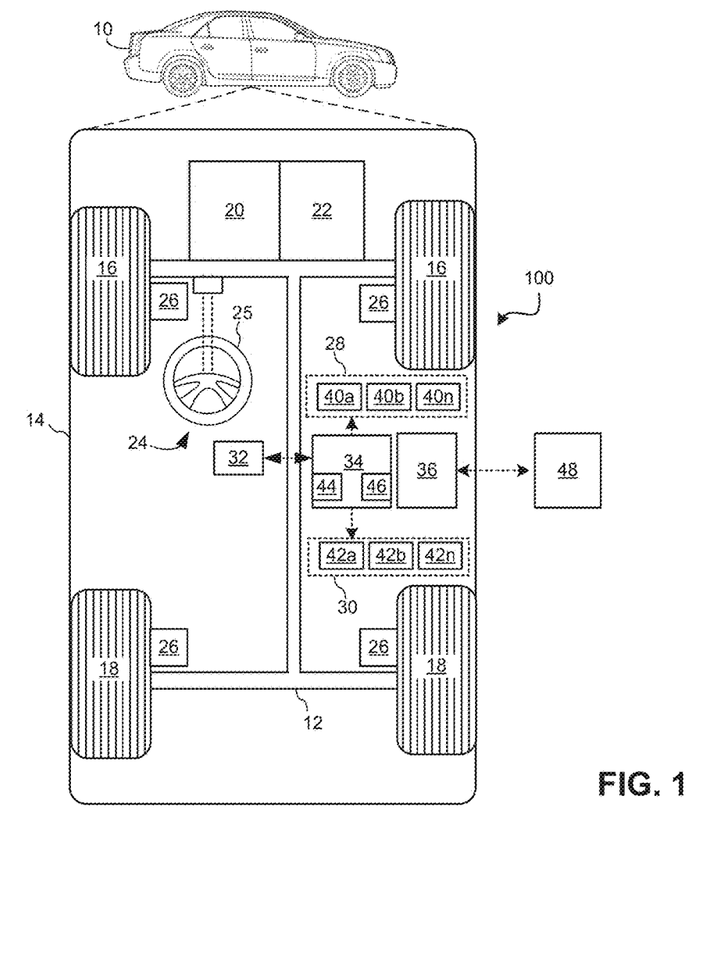
FIG. 1 is a functional block diagram illustrating an autonomous vehicle having a driving mode selection system, in accordance with various embodiments.

With reference to FIG. 1, a soundscape selection system shown generally as 100 is associated with a vehicle 10 in accordance with various embodiments. In general, soundscape selection system 100 is configured to modify vehicle parameters to provide the occupant or occupants with a set of internal sound conditions (or "soundscape") in accordance with the state of mind of the occupant or occupants. In some embodiments, a soundscape is selected to counteract the apparent state of mind of the occupant (e.g., providing soothing music and reducing engine noise for an occupant experiencing a high level of anxiety). In other embodiments, a soundscape is selected to augment the apparent state of mind of the occupant (e.g., providing louder music and/or more aggressive powertrain, engine, and transmission settings when an occupant is concerned about reaching a destination on time).

As depicted in FIG. 1, vehicle 10 generally includes a chassis 12, a body 14, front wheels 16, and rear wheels 18. The body 14 is arranged on the chassis 12 and substantially encloses components of the vehicle 10. The body 14 and the chassis 12 may jointly form a frame. The wheels 16-18 are each rotationally coupled to the chassis 12 near a respective corner of the body 14.

In various embodiments, the vehicle 10 is an autonomous vehicle and the driving mode selection system 100 is incorporated into the autonomous vehicle 10 (hereinafter referred to as the autonomous vehicle 10). The autonomous vehicle 10 is, for example, a vehicle that is automatically controlled to carry passengers from one location to another. The vehicle 10 is depicted in the illustrated embodiment as a passenger car, but it should be appreciated that any other vehicle, including motorcycles, trucks, sport utility vehicles (SUVs), recreational vehicles (RVs), marine vessels, aircraft, etc., can also be used.

In an exemplary embodiment, the autonomous vehicle 10 corresponds to a level four or level five automation system under the Society of Automotive Engineers (SAE) "J3016" standard taxonomy of automated driving levels. Using this terminology, a level four system indicates "high automation," referring to a driving mode in which the automated driving system performs all aspects of the dynamic driving task, even if a human driver does not respond appropriately to a request to intervene. A level five system, on the other hand, indicates "full automation," referring to a driving mode in which the automated driving system performs all aspects of the dynamic driving task under all roadway and environmental conditions that can be managed by a human driver. It will be appreciated, however, the embodiments in accordance with the present subject matter are not limited to any particular taxonomy or rubric of automation categories. Furthermore, driving mode selection systems in accordance with the present embodiment may be used in conjunction with any autonomous vehicle that utilizes a navigation system to provide route guidance.

As shown, the autonomous vehicle 10 generally includes a propulsion system 20, a transmission system 22, a steering system 24, a brake system 26, a sensor system 28, an actuator system 30, at least one data storage device 32, at least one controller 34, and a communication system 36. The propulsion system 20 may, in various embodiments, include an internal combustion engine, an electric machine such as a traction motor, and/or a fuel cell propulsion system. The transmission system 22 is configured to transmit power from the propulsion system 20 to the vehicle wheels 16 and 18 according to selectable speed ratios. According to various embodiments, the transmission system 22 may include a step-ratio automatic transmission, a continuously-variable transmission, or other appropriate transmission.

The brake system 26 is configured to provide braking torque to the vehicle wheels 16 and 18. Brake system 26 may, in various embodiments, include friction brakes, brake by wire, a regenerative braking system such as an electric machine, and/or other appropriate braking systems.

The steering system 24 influences a position of the vehicle wheels 16 and/or 18. While depicted as including a steering wheel 25 for illustrative purposes, in some embodiments contemplated within the scope of the present disclosure, the steering system 24 may not include a steering wheel.

The sensor system 28 includes one or more sensing devices 40a-40n that sense observable conditions of the exterior environment and/or the interior environment of the autonomous vehicle 10. The sensing devices 40a-40n might include, but are not limited to, radars, lidars, global positioning systems, optical cameras, thermal cameras, ultrasonic sensors, and/or other sensors. In some embodiments, sensing devices 40a-40n include one or more sensors capable of observing occupants of the vehicle and classifying their respective state of mind (e.g., using a trained neural network or other such classification model known in the art). Such sensing devices 40a-40n might include, for example, infrared cameras, optical cameras, audio microphones, brain activity sensors, and the like.

The actuator system 30 includes one or more actuator devices 42a-42n that control one or more vehicle features such as, but not limited to, the propulsion system 20, the transmission system 22, the steering system 24, and the brake system 26. In various embodiments, autonomous vehicle 10 may also include interior and/or exterior vehicle features not illustrated in FIG. 1, such as various doors, a trunk, and cabin features such as air, music, lighting, touchscreen display components (such as those used in connection with navigation systems), and the like.

The data storage device 32 stores data for use in automatically controlling the autonomous vehicle 10. In various embodiments, the data storage device 32 stores defined maps of the navigable environment. In various embodiments, the defined maps may be predefined by and obtained from a remote system (described in further detail with regard to FIG. 2). For example, the defined maps may be assembled by the remote system and communicated to the autonomous vehicle 10 (wirelessly and/or in a wired manner) and stored in the data storage device 32. Route information may also be stored within data device 32—i.e., a set of road segments (associated geographically with one or more of the defined maps) that together define a route that the user may take to travel from a start location (e.g., the user's current location) to a target location. As will be appreciated, the data storage device 32 may be part of the controller 34, separate from the controller 34, or part of the controller 34 and part of a separate system.

The controller 34 includes at least one processor 44 and a computer-readable storage device or media 46. The processor 44 may be any custom-made or commercially available processor, a central processing unit (CPU), a graphics processing unit (GPU), an auxiliary processor among several processors associated with the controller 34, a semiconductor-based microprocessor (in the form of a microchip or chip set), any combination thereof, or generally any device for executing instructions. The computer readable storage device or media 46 may include volatile and nonvolatile storage in read-only memory (ROM), random-access memory (RAM), and keep-alive memory (KAM), for example. KAM is a persistent or non-volatile memory that may be used to store various operating variables while the processor 44 is powered down. The computer-readable storage device or media 46 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 34 in controlling the autonomous vehicle 10.

The instructions may include one or more separate programs, each of which comprises an ordered listing of executable instructions for implementing logical functions. The instructions, when executed by the processor 44, receive and process signals from the sensor system 28, perform logic, calculations, methods and/or algorithms for automatically controlling the components of the autonomous vehicle 10, and generate control signals that are transmitted to the actuator system 30 to automatically control the components of the autonomous vehicle 10 based on the logic, calculations, methods, and/or algorithms. Although only one controller 34 is shown in FIG. 1, embodiments of the autonomous vehicle 10 may include any number of controllers 34 that communicate over any suitable communication medium or a combination of communication mediums and that cooperate to process the sensor signals, perform logic, calculations, methods, and/or algorithms, and generate control signals to automatically control features of the autonomous vehicle 10. In one embodiment, as discussed in detail below, controller 34 is configured to allow an occupant to select a driving mode based on occupant preferences, vehicle state, and occupant state.

Figure 2:
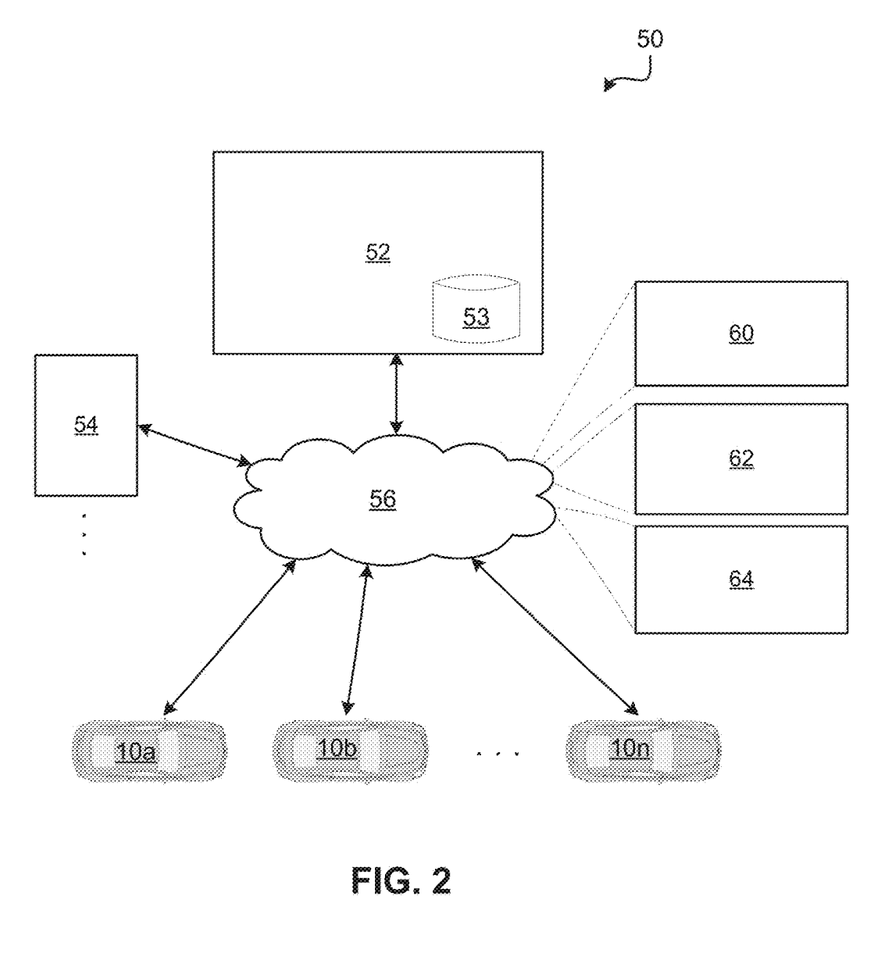
FIG. 2 is a functional block diagram illustrating a transportation system having one or more autonomous vehicles as shown in FIG. 1, in accordance with various embodiments.

The communication system 36 is configured to wirelessly communicate information to and from other entities 48, such as but not limited to, other vehicles ("V2V" communication), infrastructure ("V2I" communication), remote transportation systems, and/or user devices (described in more detail with regard to FIG. 2). In an exemplary embodiment, the communication system 36 is a wireless communication system configured to communicate via a wireless local area network (WLAN) using IEEE 802.11 standards or by using cellular data communication. However, additional or alternate communication methods, such as a dedicated short-range communications (DSRC) channel, are also considered within the scope of the present disclosure. DSRC channels refer to one-way or two-way short-range to medium-range wireless communication channels specifically designed for automotive use and a corresponding set of protocols and standards.

With reference now to FIG. 2, in various embodiments, the autonomous vehicle 10 described with regard to FIG. 1 may be suitable for use in the context of a taxi or shuttle system in a certain geographical area (e.g., a city, a school or business campus, a shopping center, an amusement park, an event center, or the like) or may simply be managed by a remote system. For example, the autonomous vehicle 10 may be associated with an autonomous vehicle based remote transportation system. FIG. 2 illustrates an exemplary embodiment of an operating environment shown generally at 50 that includes an autonomous vehicle based remote transportation system (or simply "remote transportation system") 52 that is associated with one or more autonomous vehicles 10a-10n as described with regard to FIG. 1. In various embodiments, the operating environment 50 (all or a part of which may correspond to entities 48 shown in FIG. 1) further includes one or more user devices 54 that communicate with the autonomous vehicle 10 and/or the remote transportation system 52 via a communication network 56.

The communication network 56 supports communication as needed between devices, systems, and components supported by the operating environment 50 (e.g., via tangible communication links and/or wireless communication links). For example, the communication network 56 may include a wireless carrier system 60 such as a cellular telephone system that includes a plurality of cell towers (not shown), one or more mobile switching centers (MSCs) (not shown), as well as any other networking components required to connect the wireless carrier system 60 with a land communications system. Each cell tower includes sending and receiving antennas and a base station, with the base stations from different cell towers being connected to the MSC either directly or via intermediary equipment such as a base station controller. The wireless carrier system 60 can implement any suitable communications technology, including for example, digital technologies such as CDMA (e.g., CDMA2000), LTE (e.g., 4G LTE or 5G LTE), GSM/GPRS, or other current or emerging wireless technologies. Other cell tower/base station/MSC arrangements are possible and could be used with the wireless carrier system 60. For example, the base station and cell tower could be co-located at the same site or they could be remotely located from one another, each base station could be responsible for a single cell tower or a single base station could service various cell towers, or various base stations could be coupled to a single MSC, to name but a few of the possible arrangements.

Apart from including the wireless carrier system 60, a second wireless carrier system in the form of a satellite communication system 64 can be included to provide uni-directional or bi-directional communication with the autonomous vehicles 10a-10n. This can be done using one or more communication satellites (not shown) and an uplink transmitting station (not shown). Uni-directional communication can include, for example, satellite radio services, wherein programming content (news, music, etc.) is received by the transmitting station, packaged for upload, and then sent to the satellite, which broadcasts the programming to subscribers. Bi-directional communication can include, for example, satellite telephony services using the satellite to relay telephone communications between the vehicle 10 and the station. The satellite telephony can be utilized either in addition to or in lieu of the wireless carrier system 60.

A land communication system 62 may further be included that is a conventional land-based telecommunications network connected to one or more landline telephones and connects the wireless carrier system 60 to the remote transportation system 52. For example, the land communication system 62 may include a public switched telephone network (PSTN) such as that used to provide hardwired telephony, packet-switched data communications, and the Internet infrastructure. One or more segments of the land communication system 62 can be implemented through the use of a standard wired network, a fiber or other optical network, a cable network, power lines, other wireless networks such as wireless local area networks (WLANs), or networks providing broadband wireless access (BWA), or any combination thereof. Furthermore, the remote transportation system 52 need not be connected via the land communication system 62, but can include wireless telephony equipment so that it can communicate directly with a wireless network, such as the wireless carrier system 60.

Although only one user device 54 is shown in FIG. 2, embodiments of the operating environment 50 can support any number of user devices 54, including multiple user devices 54 owned, operated, or otherwise used by one person. Each user device 54 supported by the operating environment 50 may be implemented using any suitable hardware platform. In this regard, the user device 54 can be realized in any common form factor including, but not limited to: a desktop computer; a mobile computer (e.g., a tablet computer, a laptop computer, or a netbook computer); a smartphone; a video game device; a digital media player; a component of a home entertainment equipment; a digital camera or video camera; a wearable computing device (e.g., smart watch, smart glasses, smart clothing); or the like. Each user device 54 supported by the operating environment 50 is realized as a computer-implemented or computer-based device having the hardware, software, firmware, and/or processing logic needed to carry out the various techniques and methodologies described herein. For example, the user device 54 includes a microprocessor in the form of a programmable device that includes one or more instructions stored in an internal memory structure and applied to receive binary input to create binary output. In some embodiments, the user device 54 includes a GPS module capable of receiving GPS satellite signals and generating GPS coordinates based on those signals. In other embodiments, the user device 54 includes cellular communications functionality such that the device carries out voice and/or data communications over the communication network 56 using one or more cellular communications protocols, as are discussed herein. In various embodiments, the user device 54 includes a visual display, such as a touch-screen graphical display, or other display.

The remote transportation system 52 includes one or more backend server systems, not shown), which may be cloud-based, network-based, or resident at the particular campus or geographical location serviced by the remote transportation system 52. The remote transportation system 52 can be manned by a live advisor, an automated advisor, an artificial intelligence system, or a combination thereof. The remote transportation system 52 can communicate with the user devices 54 and the autonomous vehicles 10a-10n to schedule rides, dispatch autonomous vehicles 10a-10n, and the like. In various embodiments, the remote transportation system 52 stores store account information such as subscriber authentication information, vehicle identifiers, profile records, biometric data, behavioral patterns, and other pertinent subscriber information.

In accordance with a typical use case workflow, a registered user of the remote transportation system 52 can create a ride request via the user device 54. The ride request will typically indicate the passenger's desired pickup location (or current GPS location), the desired destination location (which may identify a predefined vehicle stop and/or a user-specified passenger destination), and a pickup time. The remote transportation system 52 receives the ride request, processes the request, and dispatches a selected one of the autonomous vehicles 10a-10n (when and if one is available) to pick up the passenger at the designated pickup location and at the appropriate time. The transportation system 52 can also generate and send a suitably configured confirmation message or notification to the user device 54, to let the passenger know that a vehicle is on the way.

As can be appreciated, the subject matter disclosed herein provides certain enhanced features and functionality to what may be considered as a standard or baseline autonomous vehicle 10 and/or an autonomous vehicle based remote transportation system 52. To this end, an autonomous vehicle and autonomous vehicle based remote transportation system can be modified, enhanced, or otherwise supplemented to provide the additional features described in more detail below.

Figure 3:
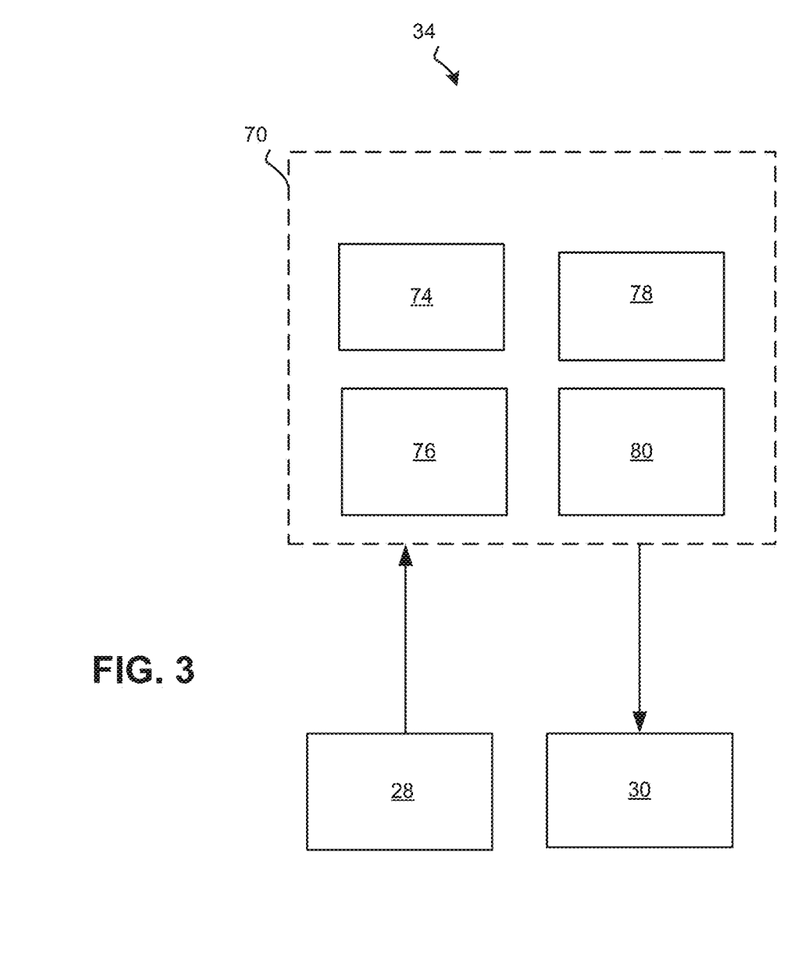
FIG. 3 is functional block diagram illustrating an autonomous driving system (ADS) associated with an autonomous vehicle, in accordance with various embodiments.

In accordance with various embodiments, controller 34 implements an autonomous driving system (ADS) 70 as shown in FIG. 3. That is, suitable software and/or hardware components of controller 34 (e.g., processor 44 and computer-readable storage device 46) are utilized to provide an autonomous driving system 70 that is used in conjunction with vehicle 10.

In various embodiments, the instructions of the autonomous driving system 70 may be organized by function or system. For example, as shown in FIG. 3, the autonomous driving system 70 can include a sensor fusion system 74, a positioning system 76, a guidance system 78, and a vehicle control system 80. As can be appreciated, in various embodiments, the instructions may be organized into any number of systems (e.g., combined, further partitioned, etc.) as the disclosure is not limited to the present examples.

In various embodiments, the sensor fusion system 74 synthesizes and processes sensor data and predicts the presence, location, classification, and/or path of objects and features of the environment of the vehicle 10. In various embodiments, the sensor fusion system 74 can incorporate information from multiple sensors, including but not limited to cameras, lidars, radars, and/or any number of other types of sensors.

The positioning system 76 processes sensor data along with other data to determine a position (e.g., a local position relative to a map, an exact position relative to lane of a road, vehicle heading, velocity, etc.) of the vehicle 10 relative to the environment. The guidance system 78 processes sensor data along with other data to determine a path for the vehicle 10 to follow. The vehicle control system 80 generates control signals for controlling the vehicle 10 according to the determined path.

In various embodiments, the controller 34 implements machine learning techniques to assist the functionality of the controller 34, such as feature detection/classification, obstruction mitigation, route traversal, mapping, sensor integration, ground-truth determination, and the like.

As mentioned briefly above, the soundscape selection system 100 of FIG. 1 is configured to modify vehicle parameters to provide the occupant or occupants with a soundscape based on the state of mind of the occupant or occupants. In some embodiments, a soundscape is selected to counteract the apparent state of mind of the occupant; in other embodiments, a soundscape is selected to augment the apparent state of mind of the occupant.

Figure 4:
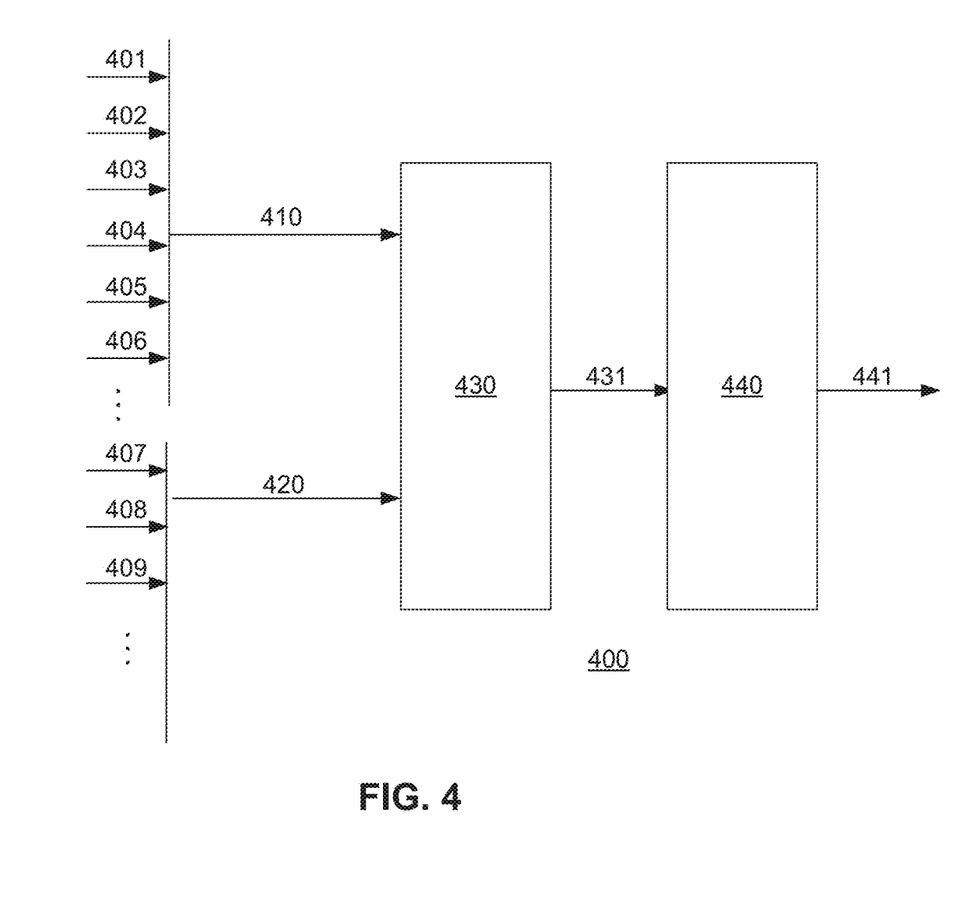
FIG. 4 is a dataflow diagram illustrating a soundscape selection system of an autonomous vehicle, in accordance with various embodiments.

Referring now to FIG. 4, an exemplary soundscape selection system 400 generally includes an occupant state of mind determination module (or simply "module") 430 that produces an output 431 indicative of a state of mind of one or more occupants of the interior of AV 10 based on biometric parameters 410 and, in some embodiments, vehicular context parameters 420. The output 431 is then used by soundscape determination module 440 to select a set of vehicle parameters 441 designed to produce the selected soundscape within AV 10 based on state of mind output 431.

As used herein, the term "soundscape" refers to the overall audio state of the interior of AV 10 as it might be experienced by one or more occupants. Thus, the soundscape might include road noise, music or other content being played by an audio system of AV 10, spoken dialog by one or more occupants, engine noise, transmission noise, traffic sounds, weather-related sounds, and the like.

A particular soundscape and its corresponding desired vehicle parameters (441) may be represented using any convenient data structure and may specify the values or set points of a wide range of vehicle parameters. In one embodiment each soundscape is represented using an associative array in which each enumerated soundscape is associated with an n-tuple of vehicle parameters and their desired settings. Without limitation, such vehicle parameters might include, for example, transmission shift points, maximum acceleration/deceleration rates, torque converter clutch slip, exhaust noise, road noise, engine mount rates, active noise cancellation, suspension softness, engine calibration adjustments, tire pressure, cylinder deactivation, route selection, media content, media volume, and the like.

Biometric parameters 410 generally include parameters (and/or parameter values) that might be used to categorize the state of mind of an occupant. In some embodiments, for example biometric parameters 410 include facial expressions (as determined, for example, via convolutional neural network techniques) 401, voice tone 402 (e.g., loud, soft, etc.), spoken utterance content 403 (e.g., profanity, key words related to distress or exasperation, etc.), body temperature 404, gestures 405 (e.g., angry hand motions, etc.), and eye characteristics 406 (e.g., dilated pupils, etc.). The determination of such parameters based the observation of a human being with a range of sensors is well known in the art, and need not be described herein.

Vehicular context parameters 420 generally include parameters (and/or parameter values) that might be used to characterize non-biometric, vehicle-related factors experienced by an occupant of the vehicle. Such vehicular context parameters 420 might include, for example, a navigation state 407—i.e., whether AV 10 is falling behind with respect to a desired time to reach a destination established by the occupant. Parameters 420 might also include traffic conditions 408 (e.g., congested, stop-and-go, freely moving, etc.), and weather conditions 409 (e.g., snow, rain, cloudy, clear, sunny, etc.).

Modules 420 and 440 may be implemented in a variety of ways, ranging from relatively simple decision trees to machine learning models that are trained via supervised, unsupervised, or reinforcement learning. A variety of machine learning techniques may be employed for this purpose, including, for example, artificial neural networks (ANN), random forest classifiers, Bayes classifiers (e.g., naive Bayes), principal component analysis (PCA), support vector machines, linear discriminant analysis, and the like.

In one embodiment, for example, module 430 is implemented as an artificial neural network that is trained via supervised learning. That is, a training set of empirically determined biometric parameters (e.g., based on the observation of test subjects driving actual vehicles) may be used as inputs to an artificial neural network while self-reported values of states of mind are used as outputs. Standard back-propagation techniques may then be used to produce the trained model for module 430.

In one embodiment, soundscape determination module 440 is implemented as a look-up table or decision tree that selects a predetermined soundscape and related vehicle parameters based on a "best fit" to the current state of mind 431 determined by module 430. In some embodiments, AV 10 provides a suitable user interface allowing the occupant to configure or otherwise customize module 440. For example, the occupant may prefer that module 440 never select a soundscape that includes loud music or which never deactivates noise cancellation. In some embodiments, a suitable user interface is presented to the user prior to engaging vehicle parameters 441 in order to confirm that the occupant wishes to change the vehicle parameters. In some embodiments, the biometric parameters 410 corresponding to an occupant positioned within the driver's seat (rather than some other occupant) is prioritized over other biometric parameters 410 when selecting a soundscape.

In general, it will be understood that various embodiments of the system 100 according to the present disclosure can include any number of sub-modules embedded within the controller 34. As can be appreciated, the sub-modules shown in FIG. 4 can be combined and/or further partitioned to similarly determine states of mind and select soundscapes. Inputs to the system 100 may be received from the sensor system 28, received from other control modules (not shown) associated with the autonomous vehicle 10, received from the communication system 36, and/or determined/modeled by other sub-modules (not shown) within the controller 34 of FIG. 1.

Figure 5:
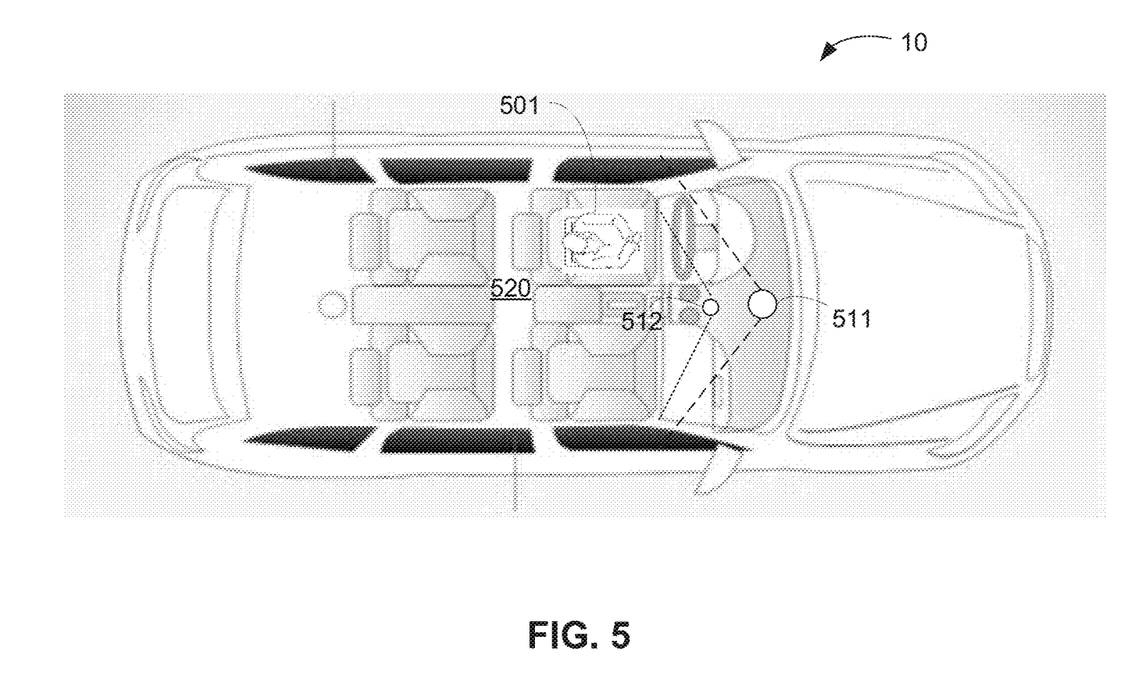
FIG. 5 is a conceptual interior view of an autonomous vehicle in accordance with various embodiments.

FIG. 5 depicts, in simplified form, the interior 520 of an exemplary vehicle 10 including an occupant 501, shown as seated in the front driver's seat. Also shown in FIG. 5 are various sensors 511 and 512 (which may be part of sensor system 28) that are configured to observed occupant 501 as well as any other occupants that may be located within interior 520 of vehicle 10. It will be understood that any number of sensors may be employed in any convenient locations, and that the illustrated embodiment is not intended to be limiting.

Sensors 511, 512 may include any type of sensor now known or later developed. In general, sensors 511, 512 are selected based on the ability to produce biometric parameters 410 of FIG. 4. In that regard, sensors 511, 512 may be infrared sensors, optical sensors, audio microphones, or any other class of sensor that is capable of producing an image or quantitative measure indicative of the state of mind of occupant 501. The data and/or signals produced by sensors 511, 512 may be processed by intermediary sub-modules (not illustrated) to produce the desired biometric parameters 410. For example, facial expression parameter 401 and gesture parameter 405 may be produced by a previously trained convolutional neural network model, as is known in art, that takes as its input an image or sequence of images and produces an output such as an integer value corresponding to an enumerated state of mind (e.g., 1="calm," 2="aggravated," 3="extremely aggravated," etc.).

In that regard, as used herein the term "state of mind" (as it related to output 431 of FIG. 4) refers to any representation of a state selected from any convenient taxonomy of such states. The number and type of such states may vary, depending upon design considerations and level of desired granularity. For example, the states may be selected from what is known as the Plutchick wheel of emotions, which may be partitioned as desired (e.g., into contiguous subregions) to generate a set of possible states of mind, which might also be combined with a quantifier parameter (e.g., to capture the extent to which the occupant displays that emotion, such as a real number in the range 0.0-1.0). Similarly, a simpler, Lovheim-cube-based representation of states may also be used in determining appropriate states of mind, as is known in the art. It will be appreciated, however, that these taxonomies are merely provided as examples, and that the range of possible embodiments is not so limited.

Figure 6:
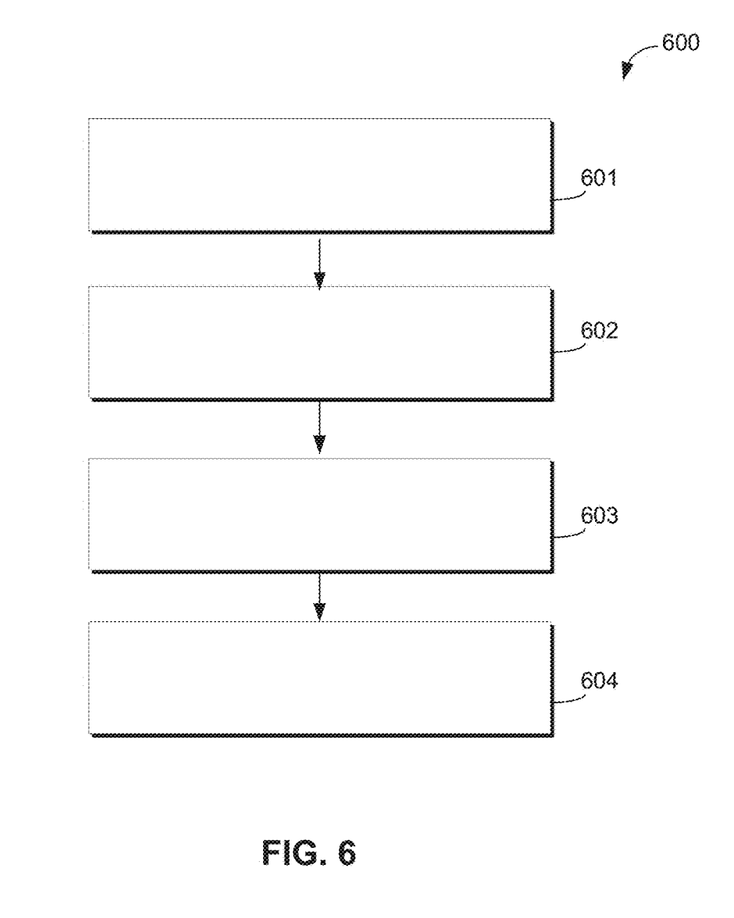
FIG. 6 is a flowchart illustrating a control method for controlling the autonomous vehicle, in accordance with various embodiments.

Referring now to FIG. 6, and with continued reference to FIGS. 1-5, the illustrated flowchart provides a control method 600 that can be performed by system 100 in accordance with the present disclosure. As can be appreciated in light of the disclosure, the order of operation within the method is not limited to the sequential execution as illustrated in FIG. 6, but may be performed in one or more varying orders as applicable and in accordance with the present disclosure. In various embodiments, methods 600 can be scheduled to run based on one or more predetermined events, and/or can run continuously during operation of the autonomous vehicle 10.

Initially, at 601, it is assumed that an autonomous vehicle path has been established based on a destination requested by occupant 501. The determination of such a path based on map data and the like is well known in the art and need not be described in detail herein.

Subsequently, at 602, biometric parameters 410 and vehicular context parameters 420 are received by module 430. That is, assuming a scenario in which occupant 501 has entered the desired destination and is seated within AV 10 during normal operation, sensors 512, 511 observe occupant 501 (e.g., via facial expression 401, body temperature 404, gestures 405, eye characteristics 406, etc.).

Based on these parameters 410 (and, in some embodiments, vehicular context parameters 420), module 430 determines (at 603) a state of mind 431 of occupant 501 (e.g., "angry", "calm", "bored", etc.). As described herein, state of mind 431 may be represented in any number of ways and may be selected from any convenient set of relevant states (i.e., states of mind that might be amenable to alteration or augmentation via an appropriate soundscape).

Finally, at 604, vehicle parameters 441 are selected based on the determined state of mind 431 in order to achieve a desired soundscape. In this regard, the selected soundscape and corresponding vehicle parameters 441 may be selected to counteract the determined state of mind 431 (e.g., by producing a quiet soundscape to calm down an angry occupant), or may be selected to augment or amplify the determined state of mind 431 (e.g., by choosing loud, aggressive music to accompany an occupant apparent eagerness to reach his or her destination more quickly).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. A method of soundscape selection in a vehicle, the method comprising:
   receiving a plurality of biometric parameters from one or more sensors provided within an interior of the vehicle;
   determining, using an artificial neural network, a state of mind of an occupant within the interior of the vehicle based on the biometric parameters and a plurality of vehicular context parameters;
   determining, using a decision tree and with a soundscape determination module including a processor, a soundscape that changes the state of mind of the occupant; and
   providing to the vehicle a set of vehicle parameters based on the selected soundscape.

2. The method of claim 1, wherein the vehicular context parameters include an estimated time that the vehicle is likely to travel along a vehicle path to a destination selected by the occupant.

3. The method of claim 1, wherein receiving a plurality of biometric parameters includes receiving a plurality of biometric parameters from at least one of an optical camera, an infrared camera, a brainwave activity sensor, and an audio microphone provided within the interior of the vehicle.

4. The method of claim 1, wherein the set of vehicle parameters include at least one of transmission shift points, maximum acceleration rate, torque converter clutch slip, exhaust noise, road noise, engine mount rates, active noise cancellation, cylinder deactivation, tire pressure, suspension adjustment, and audio media selection.

5. The method of claim 1, wherein the soundscape is determined to amplify the state of mind of the occupant.

6. The method of claim 1, wherein the soundscape is determined to counteract the state of mind of the occupant.

7. An autonomous vehicle comprising:
   one or more sensors provided within an interior of the autonomous vehicle, the one or more sensors configured to observe an occupant within the interior of the autonomous vehicle and produce a plurality of biometric parameters associated therewith;
   a state of mind determination module, including a processor, configured to determine a state of mind of an occupant within the interior of the vehicle based on the plurality of biometric parameters and a vehicular context parameters and using an artificial neural network; and
   a soundscape determination module, including the processor, configured to determine a soundscape that changes the state of mind of the occupant based on a decision tree and provide to the vehicle a set of vehicle parameters based on the selected soundscape.

8. The autonomous vehicle of claim 7, wherein the vehicular context parameters include an estimated time that the vehicle is likely to travel along a vehicle path to a destination selected by the occupant.

9. The autonomous vehicle of claim 7, wherein the plurality of biometric parameters are received from at least one of an optical camera, an infrared camera, a brainwave activity sensor, and an audio microphone provided within the interior of the vehicle.

10. The autonomous vehicle of claim 7, wherein the set of vehicle parameters include at least one of transmission shift points, maximum acceleration rate, torque converter clutch slip, exhaust noise, road noise, engine mount rates, active noise cancellation, cylinder deactivation, tire pressure, suspension adjustment, and audio media selection.

11. The autonomous vehicle of claim 7, wherein the soundscape is determined to amplify the state of mind of the occupant.

12. The autonomous vehicle of claim 7, wherein the soundscape is determined to counteract the state of mind of the occupant.

13. A system for controlling an autonomous vehicle, the system comprising:
   one or more sensors provided within an interior of the autonomous vehicle, the one or more sensors configured to observe an occupant within the interior of the autonomous vehicle and produce a plurality of biometric parameters associated therewith;
   a state of mind determination module, including a processor, configured to determine a state of mind of an occupant within the interior of the vehicle based on the plurality of biometric parameters and a vehicular context parameters and using an artificial neural network; and a soundscape determination module, including the processor, configured to determine a soundscape that changes the state of mind of the occupant based on a decision tree and provide to the vehicle a set of vehicle parameters based on the selected soundscape.

14. The system of claim 13, wherein the vehicular context parameters include an estimated time that the vehicle is likely to travel along a vehicle path to a destination selected by the occupant.

15. The system of claim 14, wherein the plurality of biometric parameters are received from at least one of an optical camera, an infrared camera, a brainwave activity sensor, and an audio microphone provided within the interior of the vehicle.

16. The system of claim 13, wherein the set of vehicle parameters include at least one of transmission shift points, maximum acceleration rate, torque converter clutch slip, exhaust noise, road noise, engine mount rates, active noise cancellation, cylinder deactivation, tire pressure, suspension adjustment, and audio media selection.

17. The system of claim 13, wherein the soundscape is determined to counteract the state of mind of the occupant.

* * * * *